United States Patent
Batista et al.

(10) Patent No.: US 12,214,123 B2
(45) Date of Patent: Feb. 4, 2025

(54) AEROSOL-GENERATING DEVICE WITH INTEGRAL HEATER ASSEMBLY

(71) Applicant: Altria Client Services LLC, Richmond, VA (US)

(72) Inventors: Rui Nuno Batista, Morges (CH); Laurent Manca, Sullens (CH)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 18/464,434

(22) Filed: Sep. 11, 2023

(65) Prior Publication Data
US 2023/0417407 A1 Dec. 28, 2023

Related U.S. Application Data

(63) Continuation of application No. 17/201,185, filed on Mar. 15, 2021, now Pat. No. 11,754,280, which is a
(Continued)

(30) Foreign Application Priority Data

May 31, 2016 (EP) .................................... 16172173

(51) Int. Cl.
*A61M 15/06* (2006.01)
*A24F 40/10* (2020.01)
(Continued)

(52) U.S. Cl.
CPC ............. *A61M 15/06* (2013.01); *A24F 40/40* (2020.01); *A24F 40/42* (2020.01); *A24F 40/46* (2020.01);
(Continued)

(58) Field of Classification Search
CPC ........ A24F 47/008; A24F 40/10; A24F 40/40; A24F 40/42; A24F 40/46; A24F 40/485;
(Continued)

(56) References Cited

U.S. PATENT DOCUMENTS 9,737,093 B2 * 8/2017 Hon .................. A24F 40/46
2005/0172976 A1 8/2005 Newman et al.
(Continued)

FOREIGN PATENT DOCUMENTS

CN 203969195 U 12/2014
CN 104720109 A 6/2015
(Continued)

OTHER PUBLICATIONS

Written Opinion for Application No. PCT/EP2017/062723 dated Aug. 10, 2017.
(Continued)

*Primary Examiner* — Joe E Mills, Jr.
(74) *Attorney, Agent, or Firm* — Harness, Dickey & Pierce, P.L.C.

(57) ABSTRACT

An electrically heated aerosol-generating device is configured for use with a consumable cartridge including a storage portion containing an aerosol-forming substrate and having a fluid permeable internal surface surrounding an open-ended passage extending through the cartridge. The device includes a housing having a cavity for receiving the cartridge and a heater assembly positioned in the cavity. The heater assembly includes an electrically conductive hollow shaft portion connected to the housing and an electric heater positioned along the hollow shaft portion and having at least one heating element for heating the aerosol-forming substrate. The hollow shaft portion defines an airflow passage forming part of an airflow pathway through the device and is arranged to extend into the open-ended passage of the
(Continued)

cartridge. The hollow shaft portion comprises a plurality of apertures, and the heating element is one or more narrow regions of the hollow shaft portion between adjacent apertures.

19 Claims, 5 Drawing Sheets

Related U.S. Application Data continuation of application No. 15/609,352, filed on May 31, 2017, now Pat. No. 10,952,471, which is a continuation of application No. PCT/EP2017/062723, filed on May 25, 2017.

(51) Int. Cl.
*A24F 40/40* (2020.01)
*A24F 40/42* (2020.01)
*A24F 40/46* (2020.01)
*A24F 40/485* (2020.01)
*F22B 1/28* (2006.01)

(52) U.S. Cl.
CPC ............ *A24F 40/485* (2020.01); *F22B 1/284* (2013.01); *A24F 40/10* (2020.01)

(58) Field of Classification Search
CPC .. F22B 1/284; A61M 11/042; A61M 15/0028; A61M 15/003; A61M 15/0036; A61M 15/06; H05B 3/06; H05B 3/58
See application file for complete search history.

(56) References Cited

U.S. PATENT DOCUMENTS

| | | |
|---|---|---|
| 2014/0190477 A1 | 7/2014 | Qiu |
| 2014/0305454 A1 | 10/2014 | Rinker et al. |
| 2015/0007835 A1 | 1/2015 | Liu |
| 2015/0090280 A1 | 4/2015 | Chen |
| 2015/0272218 A1 | 10/2015 | Chen |
| 2016/0000149 A1 | 1/2016 | Scatterday |
| 2017/0006917 A1 | 1/2017 | Alvarez |
| 2017/0119054 A1* | 5/2017 | Zinovik .................. H05B 6/02 |

FOREIGN PATENT DOCUMENTS

| | | |
|---|---|---|
| EP | 2340729 A1 | 7/2011 |
| EP | 3020292 A1 | 5/2016 |
| JP | 2014-525237 A | 9/2014 |
| JP | 2016-513453 A | 5/2016 |
| RU | 2566914 C1 | 10/2015 |
| WO | WO-2009/132793 A1 | 11/2009 |
| WO | WO-2013/098395 A1 | 7/2013 |
| WO | WO-2014/201432 A1 | 12/2014 |
| WO | WO-2015/177044 A1 | 11/2015 |

OTHER PUBLICATIONS

International Search Report for corresponding Application No. PCT/EP2017/062723 dated Dec. 7, 2017.
International Preliminary Examination Report for corresponding Application No. PCT/EP2017/062723 dated May 11, 2018.
Extended European Search Report for European Application No. 16172173.3 dated Dec. 6, 2016.
Office Action for Japanese Application No. 2018-562994 dated Jun. 3, 2021 and English translation.
Office Action for Japanese Application No. 2021-111276 dated Aug. 10, 2022 and English translation.
Notice of Allowance for Japanese Application No. 2021-111276 dated Jan. 30, 2023 and English translation.
Notice of Allowance for Korean Application No. 10-2018-7032438 dated Nov. 21, 2022 and English translation.
Notice of Allowance for Korean Application No. 10-2023-7005644 dated Dec. 22, 2023 and English translation.
Office Action for Russian Application No. 2020128015 dated Dec. 13, 2023 and English translation.
Office Action for Chinese Application No. 202110730963.7 dated Jul. 3, 2024 and English translation.

* cited by examiner

AEROSOL-GENERATING DEVICE WITH INTEGRAL HEATER ASSEMBLY

CROSS-REFERENCE TO RELATED APPLICATIONS

This is a continuation of U.S. application Ser. No. 17/201,185, filed on Mar. 15, 2021, which is a continuation of U.S. application Ser. No. 15/609,352, filed on May 31, 2017, which is a continuation of and claims priority to PCT/EP2017/062723, filed on May 25, 2017, and further claims priority to EP 16172173.3, filed on May 31, 2016, the disclosures of each of which are hereby incorporated by reference in their entirety.

BACKGROUND

Field

The present disclosure relates to an aerosol-generating device for use with a consumable cartridge. In addition, the present disclosure relates to an electrically heated aerosol-generating device for use with a consumable cartridge having an internal passage and containing an aerosol-forming substrate. The present disclosure also relates to consumable cartridges for use with aerosol-generating devices, electrically heated aerosol-generating systems comprising an electrically heated aerosol-generating device and a consumable cartridge, and kits for an electrically heated aerosol-generating system comprising an electrically heated aerosol-generating device and a plurality of consumable cartridges.

Description of Related Art

Electrically heated smoking systems that are handheld and operate by heating an aerosol-forming substrate in an aerosol-generating article, or cartridge, are known in the art. An electrically heated smoking system may comprise a shell and a replaceable mouthpiece. The shell comprises an electric power supply and electric circuitry. The mouthpiece comprises a liquid storage portion and a capillary wick having a first end and a second end. The first end of the wick extends into the liquid storage portion for contact with liquid therein. The mouthpiece also comprises a heating element for heating the second end of the capillary wick, an air outlet, and an aerosol-forming chamber between the second end of the capillary wick and the air outlet. The wick and heating element form a heater assembly by which the aerosol-forming substrate is heated. The heating element is typically a coil of wire that is wound around the wick. When the shell and mouthpiece are engaged, the heating element is in electrical connection with the power supply via the circuitry, and a flow route for air is defined from at least one air inlet to the air outlet via the aerosol-forming chamber. In use, liquid is transferred from the liquid storage portion towards the heating element by capillary action in the wick. Liquid at the second end of the capillary wick is vaporised by the heating element. The supersaturated vapour created, is mixed and carried in the air-flow from the at least one air inlet to the aerosol-forming chamber. In the aerosol-forming chamber, the vapour condenses to form an aerosol, which is carried towards the air outlet.

SUMMARY

The specific characteristics of the heater assembly are important for achieving the required functional performance. Therefore, the ability to accurately and consistently produce heater assemblies is important in maintaining consistent performance between different aerosol-generating systems of the same type. For example, in heater assemblies having a heater coil, the heater coils should be produced with the same dimensions to reduce product-to-product variability.

According to some example embodiments, there is provided an electrically heated aerosol-generating device for use with a cartridge (e.g., consumable cartridge) comprising a storage portion containing an aerosol-forming substrate, the storage portion having a fluid permeable internal surface surrounding an open-ended passage extending through the cartridge, the device comprising a housing having a cavity for receiving at least a portion of the cartridge; and a heater assembly positioned in the cavity, the heater assembly comprising: an electrically conductive hollow shaft portion connected to the housing and defining an airflow passage forming part of an airflow pathway through the device, the hollow shaft portion being arranged to extend into the open-ended passage of a cartridge received in the cavity, and at least one electric heater positioned along the hollow shaft portion, the electric heater comprising at least one heating element for heating the aerosol-forming substrate of a cartridge received in the cavity, wherein the hollow shaft portion comprises a plurality of apertures, and wherein the at least one heating element is formed by one or more narrow regions of the hollow shaft portion between adjacent apertures.

Having a heater assembly with one or more integral electric heaters may require fewer manufacturing steps and allow the heater assembly to be manufactured on an automated assembly line. This may allow aerosol-generating devices to be manufactured more quickly, simply, and with relatively high repeatability and consistency. For instance, the aerosol-generating devices may be simplified, less expensive, and more robust than devices in which the heater assembly comprises complicated and potentially fragile connections. Additionally, by providing the electric heaters as part of the device, cartridges for use with the device may be simplified, less expensive, and more robust than cartridges which include an electric heater. Accordingly, reducing the cost of cartridges, even if it requires a more expensive device, can lead to significant cost savings for both manufacturers and consumers.

The hollow shaft portion has an internal airflow passage forming part of an airflow pathway through the device. With this arrangement, the hollow shaft portion may provide a support for the at least one electric heater as well as providing an airflow channel. This allows for a device which is compact and facilitates cost-effective high volume manufacturing. Having an airflow passage within the hollow shaft portion may help to minimise heat loss from the device and allow the housing of the device to be more easily maintained at a temperature which is comfortable to hold. Furthermore, vaporised aerosol-forming substrate in the air flow through the hollow shaft portion can begin to cool within the airflow passage to form an aerosol, allowing the overall length of the device to be reduced.

The apertures may be formed in the hollow shaft portion after the hollow shaft portion has been formed, for example by punching, drilling, milling, erosion, electro erosion, cutting, or laser cutting. The apertures may be formed integrally with the hollow shaft portion at the time of forming the hollow shaft portion, for example by casting or moulding the hollow shaft portion with the apertures or by forming the hollow shaft portion with the apertures in a deposition process, such as electrodeposition.

As used herein, "electrically conductive" means formed from a material having a resistivity of $1\times10^{-4}$ Ωm, or less. As used herein, "electrically insulating" means formed from a material having a resistivity of $1\times10^{4}$ Ωm or more. The at least one electric heater may be arranged on the hollow shaft portion in any suitable manner. The at least one electric heater may circumscribe the hollow shaft portion. This may allow for more even heating of the aerosol-forming substrate in the cartridge relative to devices in which the at least one electric heater does not circumscribe the hollow shaft portion. The at least one electric heater may circumscribe the hollow shaft portion continuously. The at least one electric heater may circumscribe the hollow shaft portion discontinuously in the form of a plurality of electric heaters spaced apart in the circumferential direction of the hollow shaft portion. In other example embodiments, the at least one electric heater may extend around only part of the circumference of the hollow shaft portion.

The at least one electric heater may extend along only part of the length of the hollow shaft portion. In this manner, only a portion of the length of the hollow shaft portion is occupied by the at least one electric heater. The at least one electric heater may extend along substantially the entire length of the hollow shaft portion. This arrangement may allow for more even heating of the aerosol-forming substrate in the cartridge relative to devices in which the at least one electric heater extends along only part of the length of the hollow shaft portion. It may also allow the device to heat parts of a cartridge to which would not be heated by devices in which the at least one electric heater extends along only part of the length of the hollow shaft portion, enabling more of the aerosol-forming substrate in each cartridge to be vaporised, reducing waste. The at least one electric heater may extend continuously along substantially the entire length of the hollow shaft portion. The at least one electric heater may extend along substantially the entire length of the hollow shaft portion discontinuously in the form of a plurality of electric heaters spaced apart in the longitudinal direction of the hollow shaft portion.

The at least one electric heater may circumscribe the hollow shaft portion and extend along substantially the entire length of the hollow shaft portion.

The heater assembly may comprise a single electric heater comprising at least one heating element for heating the aerosol-forming substrate of a cartridge received in the cavity. Alternatively, the heater assembly may comprise a plurality of electric heaters spaced apart along the length of the hollow shaft portion for heating the aerosol-forming substrate of a cartridge received in the cavity.

This arrangement may allow for more even heating of the aerosol-forming substrate in the cartridge relative to devices in which only one electric heater is provided or in which a plurality of electric heaters are provided but which are not spaced along the length of the hollow shaft portion. It may also allow the device to heat parts of a cartridge to which would not be heated by devices having only a single heater, enabling more of the aerosol-forming substrate in each cartridge to be vaporised, reducing waste. Additionally, when used with cartridges having a plurality of different aerosol-forming substrates stored separately, the plurality of longitudinally spaced apart electric heaters may allow separate heating of the different aerosol-forming substrates to produce an aerosol with particularly desirable characteristics.

Where the heater assembly comprises a plurality of electric heaters spaced apart along the length of the hollow shaft portion, one or more of the electric heaters may be aligned in the longitudinal direction of the hollow shaft portion. For example, the plurality of electric heaters may comprise a first row of electric heaters aligned in the longitudinal direction of the hollow shaft portion and one or more further rows of electric heaters aligned in the longitudinal direction of the hollow shaft portion and spaced apart from the first row second around the circumference of the hollow shaft portion.

Where the heater assembly comprises a plurality of electric heaters spaced apart along the length of the hollow shaft portion, the electric heaters may be offset from each other around the circumference of the hollow shaft portion.

The plurality of electric heaters may be electrically isolated from each other so that each can be heated independently. With this arrangement, the heater assembly may allow the supply of electrical power to each of the electric heaters to be varied, for example according to which of the electric heaters is in the best condition to generate aerosol in the most effective way. This may help to minimise variations in aerosol properties caused by variations in the distribution of the aerosol-forming substrate within the cartridge. It may also reduce overall energy consumption of the device by allowing the energy draw of the electric heaters to be selected in the most effective manner. By electrically isolating each of the plurality of electric heaters so that each can be heated independently, the risk of damage to one or more of the electric heaters due to overheating may be reduced by selectively reducing the supply of power to one or more of the electric heaters.

The at least one electric heater may be coupled to an electrical power supply in any suitable manner. For example, the heater assembly may comprise a plurality of electrical conductors extending along the length of the hollow shaft portion for coupling the at least electric heater to an electrical power supply. The plurality of electrical conductors may comprise a plurality of wires, or a plurality of strips of electrically conductive material attached to the hollow shaft portion for example by deposition, printing, or by laminating with the hollow shaft portion as a laminated foil. The laminate foil may then be shaped or folded to form the hollow shaft portion.

In an example embodiment, the hollow shaft portion is at least partially divided into a plurality of electrically isolated sections for coupling the at least one electric heater to an electrical power supply, wherein the electrically isolated sections are electrically isolated from each other by one or more insulating gaps formed in the hollow shaft portion. Where the heater assembly comprises a plurality of electric heaters, the hollow shaft portion may be at least partially divided into a plurality of electrically isolated sections for coupling the plurality of electric heaters to an electrical power supply, wherein the electrically isolated sections are electrically isolated from each other by one or more insulating gaps formed in the hollow shaft portion. Thus, the at least one electric heater, or the plurality of electric heaters, and the means for coupling the at least electric heater to an electrical power supply are integral to the hollow shaft portion. With this arrangement, the hollow shaft portion may perform the additional function of coupling the at least one electric heater to an electric power supply without the need for additional manufacturing steps to attach additional conductive components to the heater assembly.

The insulating gaps may be air gaps. That is, the insulating gaps may be a simple spacing between adjacent electrically isolated sections. In other examples, one or more of the insulating gaps may be filled or partially filled with an electrically insulating material.

The insulating gaps may be formed in the hollow shaft portion, to at least partially divide the hollow shaft portion into a plurality of electrically isolated sections, after the hollow shaft portion has been formed, for example by punching, drilling, milling, erosion, electro erosion, cutting, or laser cutting. The insulating gaps may be formed integrally with the hollow shaft portion at the time of forming the hollow shaft portion, for example by casting or moulding the hollow shaft portion with the insulating gaps or by forming the hollow shaft portion using a deposition process, such as electrodeposition.

The hollow shaft portion may have a piercing surface at its distal end. This allows the hollow shaft portion to pierce an end of a cartridge inserted into the cavity, for example by piercing a frangible seal at the end of a cartridge during insertion of the cartridge. Thus, the hollow shaft portion may function as an elongate piercing member. To facilitate piercing of the cartridge, or a portion of the cartridge, such as a frangible seal, the distal end of the hollow shaft portion at which the piercing surface is located may have a cross-sectional area that is smaller than the cross-sectional area of the region of the hollow shaft portion immediately proximal of the piercing surface. In an example embodiment, the cross-sectional area of the hollow shaft portion narrows towards a tapered tip at the distal end of the hollow shaft portion. For instance, the cross-sectional area of the hollow shaft portion may narrow towards a point at the distal end of the hollow shaft portion.

The heater assembly may be formed from a number of separate components which are assembled together to form the heater assembly. Alternatively, the heater assembly is a single, unitary component. This may require fewer manufacturing steps than existing systems in which the heater assembly is formed from a plurality of separate components. This may also allow the heater assembly to be manufactured on an automated assembly line, so that such devices can be manufactured more quickly with high repeatability.

The device may comprise an electrical power supply connected to the heater assembly. For example, the power supply may be a battery such as a lithium iron phosphate battery, or another form of charge storage device such as a capacitor. The power supply may be located within the housing. The power supply may require recharging and may have a capacity that allows for the storage of enough energy for one or more smoking experiences. For example, the power supply may have sufficient capacity to allow for the continuous generation of aerosol for a period of around six minutes or for a period that is a multiple of six minutes. In another example, the power supply may have sufficient capacity to allow for a predetermined number of puffs or discrete activations.

The devices may comprise electric circuitry connected to the heater assembly and to an electrical power source. The electric circuitry may comprise a microprocessor, which may be a programmable microprocessor, a microcontroller, or an application specific integrated chip (ASIC) or other electronic circuitry capable of providing control. The electric circuitry may comprise further electronic components. The electric circuitry may be configured to regulate a supply of current to the heater assembly. Current may be supplied to the heater assembly continuously following activation of the device or may be supplied intermittently, such as on a puff by puff basis. The electric circuitry may comprise DC/AC inverter, which may comprise a Class-D or Class-E power amplifier.

The device may comprise an electric power supply connected to the heater assembly and electric circuitry connected to the power supply and to the heater assembly.

Where the heater assembly comprises a plurality of electric heaters which are spaced along the length of the hollow shaft portion, the electric circuitry may be configured to measure one or more electrical parameters of the plurality of electric heaters and to calculate an estimated remaining amount of aerosol-forming substrate in a cartridge received in the cavity, or an estimated distribution of aerosol-forming substrate in the cartridge, based on the measured electrical parameters.

As used herein, the term "electrical parameter" is used to describe an electrical property, value, or attribute that can be quantified by measurement, for example, resistivity, conductivity, impedance, capacitance, current, voltage, and resistance.

With this arrangement, the electric heaters may have dual functionality: heating and sensing. This may allow the device to determine at any time an estimate of the state of the aerosol-forming substrate remaining in the cartridge. From this, the device may be operated differently by the electric circuitry to maintain desirable aerosol properties or to provide information as to the current state of the aerosol-forming substrate to allow the appropriate action to be taken, such as changing the cartridge or the orientation of the device, to avoid an adverse effect on aerosol characteristics.

In such example embodiments, the electric circuitry may be configured to separately measure the one or more electrical parameters of each of the plurality of electric heaters and to calculate the estimated remaining amount, or the estimated distribution, or the estimated remaining amount and the estimated distribution, based on differences in the measured electric parameters of two or more of the plurality of electric heaters.

Where the device comprises a power supply connected to the heater assembly and electric circuitry connected to the power supply and to the heater assembly, the device may further comprise an indicator connected to power supply. The electric circuitry may be configured to operate the indicator in response to the estimated remaining amount or the estimated distribution. The indicator may have any suitable configuration, for example the indicator may be for example a display, an audio output, a haptic output, or any combination thereof. This may allow the device to convey information regarding the estimated remaining amount or the estimated distribution, or both, of liquid aerosol-forming substrate in the cartridge.

The electric circuitry may be configured to operate the indicator when the estimated remaining amount falls below a threshold value to provide an alert or otherwise prompt the replacement of the cartridge. The control circuitry may also be configured to operate the indicator when the estimated distribution suggests that device has been held at a particular angle for too long so that a prompt is provided to alter the orientation of the device, at least temporarily, so that the aerosol-forming substrate may be redistributed in the storage portion.

The control circuitry may be configured to provide information about the estimated remaining amount or estimated distribution via a communication link with a separate device, such as a smartphone, swart-watch, tablet, desktop computer, or similar device.

Where the device comprises electric circuitry connected to a power source and configured to measure one or more electrical parameters of the plurality of electric heaters and to calculate an estimated remaining amount or estimated distribution, the electric circuitry may be further configured to control a supply of power to one or more of the plurality of electric heaters separately in response to the estimated remaining amount or the estimated distribution.

This may allow the device to determine which of the electric heaters is in the best condition to generate aerosol in the most effective way and to vary the supply of power accordingly. This may help to minimise variations in aerosol properties caused by variations in the distribution of the aerosol-forming substrate within the cartridge. It may also reduce overall energy consumption of the device by allowing the energy draw of the electric heaters to be selected in the most effective manner. The electric circuitry may be configured to increase the supply of power to one or more of the plurality of electric heaters in response to the estimated remaining amount or the estimated distribution.

The electric circuitry may be configured to reduce the supply of power to one or more of the plurality of electric heaters in response to the estimated remaining amount or the estimated distribution.

This may allow the energy consumption of one or more of the electric heaters to be selectively reduced, for example where the estimated remaining amount or estimated distribution indicates that a particular electric heater is not well placed to generate an aerosol. It may also reduce the risk of damage to the electric heaters due to overheating, for example where a liquid aerosol-forming substrate is used and the electrical parameters indicate that one or more of the electric heaters is dry or partially dry.

The electric circuitry may be configured to reduce or increase the supply of power to one or more of the plurality of electric heaters in response to the estimated remaining amount or the estimated distribution. The electric circuitry may be configured to reduce the supply of power to one or more of the plurality of electric heaters while simultaneously increasing the supply of power to a different one or more of the plurality of electric heaters, in response to the estimated remaining amount or the estimated distribution.

As used herein, the term "aerosol-generating device" refers to a device that interacts with an aerosol-generating article, such as a consumable cartridge, to generate an aerosol.

The aerosol-generating device may be portable. The aerosol-generating device may have a size comparable to a cigar or cigarette. The aerosol-generating device may have a total length between approximately 30 mm and approximately 150 mm. The aerosol-generating device may have an external diameter between approximately 5 mm and approximately 30 mm.

The heater assembly may be fixed to, or integral with, the housing of the device. In other example embodiments, the heater assembly may be removably fastened to the housing. This may allow the heater assembly to be at least partially removed from the device, for example for maintenance or cleaning or to enable replacement of the heater assembly. The heater assembly may be removable coupled to the housing by one or more electrical and mechanical connection means.

The heater assembly comprises one or more electric heaters. For example, the heater assembly may comprise one, two, three, four, five, six, or more electric heaters arranged in the hollow shaft portion. Where the heater assembly comprises a plurality of electric heaters, the electric heaters may be spaced along the length of the hollow shaft portion. Each electric heater comprises at least one heating element. Each electric heater may comprise more than one heating element, for example two, or three, or four, or five, or six, or more heating elements. The heating element or heating elements may be arranged appropriately so as to most effectively heat the aerosol-forming substrate of a cartridge inserted into the cavity of the main housing.

The heating elements may have a diameter of between 0.10 and 0.15 mm (e.g., approximately 0.125 mm). The hollow shaft portion may be formed from an electrically resistive metal, such as 904 or 301 stainless steel. Examples of other suitable metals include titanium, zirconium, tantalum and metals from the platinum group. Examples of other suitable metal alloys include, Constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation, 1999 Broadway Suite 4300, Denver Colorado.

The at least one heating element may operate by resistive heating. In other words the material and dimensions of the heating element may be chosen so that when a particular current is passed through the heating element the temperature of the heating element is raised to a desired temperature. The current through the heating element may be applied by conduction from a battery or may be induced in the heating element by the application of a variable magnetic field around the heating element.

The at least one heating element of each electric heater may be formed by one or more narrow regions of the hollow shaft portion between adjacent apertures in the hollow shaft portion. The apertures may have a width of about 10 microns to about 100 microns (e.g., from about 10 microns to about 60 microns). In an example embodiment, the apertures give rise to capillary action, so that in use, a material, for example, liquid to be vaporized, is drawn into the apertures, increasing the contact area between the electric heater and the liquid. As used herein, the term "length of an aperture" refers to the dimension of the aperture along its longitudinal direction. That is, in the direction of its maximum dimension. The term "width of an aperture" refers to the dimension of the aperture in a direction transverse to its length.

The hollow shaft portion may be formed from a single tubular body. In some example embodiments, the hollow shaft portion may be formed from first and second hollow shaft portions which are fixed to the housing, extend along the same longitudinal axis, and meet at a junction. In such example embodiments, the housing may comprise a main housing in which the cavity is formed and a closure body arranged to engage with the main housing to close the cavity, wherein the first hollow shaft portion is connected to the main housing and the second hollow shaft portion is connected to the closure body. The closure body may function as a lid for closing the cavity. For instance, the closure body may form a mouthpiece portion by which air can be drawn through the airflow pathway of the aerosol-generating device.

The first and second hollow shaft portions may have a first and second piercing surfaces at their respective distal ends. This may allow the first and second hollow shaft portions to pierce an end of a cartridge inserted into the cavity, for example by piercing frangible seals at either end of a cartridge during insertion of the cartridge. Thus, the hollow shaft portion may function as an elongate piercing member. To facilitate piercing of the cartridge, or a portion of the cartridge, such as a frangible seal, the distal ends of the first and second hollow shaft portions at which the piercing surfaces are located have a cross-sectional area that is smaller than the cross-sectional area of the region of the respective hollow shaft portion immediately proximal of the piercing surface. In an example embodiment, the cross-sectional area of each hollow shaft portion narrows towards a tapered tip at its distal end. For instance, the cross-sectional area of each hollow shaft portion may narrow towards a point at its distal end.

Having a two-part hollow shaft portion with piercing surfaces may allow seals at either ends of a cartridge to be more easily broken. Without wishing to be bound by theory, it is believed that by breaking the seals towards the centre of the cartridge, the seals are prevented from moving away from the hollow shaft portions and the stresses exerted by the first and second piercing surfaces are higher, causing the seals to break more easily.

Where the first and second hollow shaft portions are sized to meet at a junction, the distal ends of the first and second hollow shaft portions may be co-operatively shaped such that a seal is formed around the junction. With this arrangement, air flow may be substantially confined to the internal airflow passage through the elongate piercing assembly, rather than passing into the storage portion of the cartridge, thereby facilitating the delivery of a consistent aerosol. The distal ends of the first and second hollow shaft portions may have any suitable, co-operative piercing shape. In an example embodiment, the distal end of one of the first and second hollow shaft portions has an inwardly tapering outer surface and the distal end of the other one of the first and second hollow shaft portions has an outwardly tapering inner surface, the inner and outer surfaces being shaped such that the inwardly tapering outer surface fits within the outwardly tapering inner surface to form the seal when the closure body is engaged with the main housing. This may allow the first and second hollow shaft portions to be mated with more ease. For example, the distal end of the first hollow shaft portion may have an inwardly tapering outer surface and the distal end of the second hollow shaft portion may have an outwardly tapering inner surface, the inner and outer surfaces being shaped such that the inwardly tapering outer surface fits within the outwardly tapering inner surface to form the seal when the closure body is engaged with the main housing.

The housing may be elongate. The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. The material may be light and non-brittle.

The housing may comprise a mouthpiece. The mouthpiece may comprise at least one air inlet and at least one air outlet. The mouthpiece may comprise more than one air inlet. One or more of the air inlets may reduce the temperature of the aerosol and the concentration of the aerosol. As used herein, the term "mouthpiece" refers to a portion of an aerosol-generating device upon which a negative pressure is applied to draw out an aerosol generated by the aerosol-generating device from an aerosol-generating article received in the cavity of the housing.

According to some example embodiments, there is provided an electrically heated aerosol-generating system comprising an aerosol-generating device as described above, and a consumable cartridge comprising a storage portion containing an aerosol-forming substrate, the storage portion having a fluid permeable internal surface surrounding an open-ended passage extending through the cartridge.

As used herein, the term "fluid permeable surface" refers to a surface that allows liquid or gas to permeate through it. The internal surface may have a plurality of openings formed in it to allow fluid to permeate through it.

The system comprises a consumable cartridge. The consumable cartridge may be removably coupled to the aerosol-generating device. As used herein, the term 'removably coupled' is used to mean that the cartridge and device can be coupled and uncoupled from one another without significantly damaging either the device or cartridge. The cartridge may be removed from the aerosol-generating device when the aerosol-forming substrate has been consumed. The cartridge may be disposable. The cartridge may be reusable. The cartridge may be refillable with aerosol-forming substrate. The cartridge may be replaceable in the aerosol-generating device.

The aerosol-generating system may comprise an aerosol-forming chamber in which an aerosol forms from a super-saturated vapour. An air inlet, air outlet, and the chamber may be arranged so as to define an airflow route from the air inlet to the air outlet via the aerosol-forming chamber, so as to convey the aerosol to the air outlet. The aerosol-forming chamber may be defined by one or both of the cartridge and the aerosol-generating device.

As used herein, the term 'aerosol-forming substrate' relates to a substrate capable of releasing volatile compounds that can form an aerosol. Such volatile compounds may be released by heating the aerosol-forming substrate. An aerosol-forming substrate may be part of an aerosol-generating article, such as a cartridge, or smoking article.

The aerosol-forming substrate may be an aerosol-forming liquid. As used herein, the terms "aerosol-forming liquid" and "liquid aerosol-forming substrate" are interchangeable. The storage portion may comprise a capillary wick forming part or all of the internal surface for transporting liquid aerosol-forming substrate from the storage portion to the heater assembly.

The storage portion may contain a single aerosol-forming substrate. Alternatively, the storage portion may contain two or more aerosol-forming substrates that are stored separately. For example, the storage portion may contain three aerosol-forming substrates stored separately, four aerosol-forming substrates stored separately, five aerosol-forming substrates stored separately, or six or more aerosol-forming substrates stored separately. Where the storage portion contains two or more aerosol-forming substrates stored separately, the heater assembly may comprise a plurality of electric heaters spaced along the length of the elongate piercing assembly, the plurality of electric heaters including at least one electric heater for each of the aerosol-forming substrates, each of the electric heaters being configured to heat its corresponding aerosol-forming substrate. This may allow the aerosol-forming substrates to be heated independently.

The storage portion of the consumable cartridge may contain first and second aerosol-forming substrates stored separately and the heater assembly may comprise a plurality of electric heaters spaced along the length of the elongate piercing assembly, the plurality of electric heaters comprising a first electric heater for heating the first aerosol-forming substrate to form a first aerosol and a second electric heater for heating the second aerosol-forming substrate to form a second aerosol.

The storage portion may be compressible and the diameter of the open-ended passage extending through the cartridge is less than the outer diameter of the hollow shaft portion. With this arrangement, the storage portion may be radially compressed by the heater assembly to ensure a tight fit between the cartridge and the hollow shaft portion. This may facilitate contact between the electric heater and the aerosol-forming substrate in the storage portion to allow consistent aerosol properties. It may also restrict or eliminate air flow between the cartridge and the outside of the hollow shaft portion, thereby facilitating the delivery of a consistent aerosol.

The aerosol-forming substrate may be an aerosol-forming liquid.

Where the aerosol-forming substrate is an aerosol-forming liquid, the storage portion may comprise a capillary wick for transporting the aerosol-forming liquid to the heater assembly, the capillary wick forming all or part of the internal surface.

The upstream and downstream ends of the cartridge may be capped by frangible seals. The cartridge may further include a sealing ring at one or both of the upstream and downstream ends of the open-ended passageway.

The cartridge may comprise a first sealed compartment comprising a first aerosol-forming substrate and a second sealed compartment comprising a second aerosol-forming substrate. The first compartment and the second compartment may be arranged in series from the upstream end to the downstream end of the cartridge. For example, the second compartment may be arranged to be downstream from the first compartment. Each of the first compartment and the second compartment may comprise a frangible barrier at each end. Each frangible barrier may be made from metal film (e.g., aluminium film). The first compartment and the second compartment of the cartridge may abut one another. The first compartment and the second compartment may be spaced apart. The volume of the first compartment and the second compartment may be the same or different. For instance, the volume of the second compartment may be greater than the volume of the first compartment.

The storage portion may form an annular space surrounding the internal open-ended passage. The cartridge may have a generally cylindrical shape and may have any desired cross-section, such as a circular, hexagonal, octagonal, or decagonal cross-section. The storage portion may comprise a tubular porous element in which a liquid aerosol-forming substrate is absorbed. The storage portion may comprise a capillary wick and a capillary material containing liquid aerosol-forming substrate. The capillary wick may define the internal surface surrounding the open-ended passage. A capillary material is a material that actively conveys liquid from one end of the material to another. The capillary material may be oriented in the storage portion to convey liquid aerosol-forming substrate to the open-ended passage. The capillary material may have a fibrous structure. The capillary material may have a spongy structure. The capillary material may comprise a bundle of capillaries. The capillary material may comprise a plurality of fibres. The capillary material may comprise a plurality of threads. The capillary material may comprise fine bore tubes. The capillary material may comprise a combination of fibres, threads and fine-bore tubes. The fibres, threads and fine-bore tubes may be generally aligned to convey liquid to the electric heater. The capillary material may comprise sponge-like material. The capillary material may comprise foam-like material. The structure of the capillary material may form a plurality of small bores or tubes, through which the liquid can be transported by capillary action.

The capillary material may comprise any suitable material or combination of materials. Examples of suitable materials are a sponge or foam material, ceramic- or graphite-based materials in the form of fibres or sintered powders, foamed metal or plastics materials, a fibrous material, for example made of spun or extruded fibres, such as cellulose acetate, polyester, or bonded polyolefin, polyethylene, terylene or polypropylene fibres, nylon fibres or ceramic. The capillary material may be made of a polymeric compound, including medical grade polymers such as ALTUGLAS® Medical Resins Polymethylmethacrylate (PMMA), Chevron Phillips K-Resin® Styrene-butadiene copolymer (SBC), Arkema special performance polymers Pebax®, Rilsan®, and Rilsan® Clear, DOW (Health+™) Low-Density Polyethylene (LDPE), DOW™ LDPE 91003, DOW™ LDPE 91020 (MFI 2.0; density 923), ExxonMobil™ Polypropylene (PP) PP1013H1, PP1014H1 and PP9074MED, Trinseo CALIBRE™ Polycarbonate (PC) 2060-SERIES. The capillary material may be made of a metallic alloy, for example aluminium or stainless steel medical grade alloys. The capillary material may have any suitable capillarity and porosity so as to be used with different liquid physical properties. The liquid aerosol-forming substrate has physical properties, including but not limited to viscosity, surface tension, density, thermal conductivity, boiling point and atom pressure, which allow the liquid to be transported through the capillary material by capillary action. The capillary material may be configured to convey the aerosol-forming substrate to the atomiser.

The aerosol-forming substrate may be an aerosol-forming liquid. In such example embodiments, the storage portion may be a liquid storage portion for storing the aerosol-forming liquid.

The liquid aerosol-forming substrate may comprise nicotine. The nicotine containing liquid aerosol-forming substrate may be a nicotine salt matrix. The liquid aerosol-forming substrate may comprise plant-based material. The liquid aerosol-forming substrate may comprise tobacco. The liquid aerosol-forming substrate may comprise a tobacco-containing material containing volatile tobacco flavour compounds, which are released from the aerosol-forming substrate upon heating. The liquid aerosol-forming substrate may comprise homogenised tobacco material. The liquid aerosol-forming substrate may comprise a non-tobacco-containing material. The liquid aerosol-forming substrate may comprise homogenised plant-based material.

The liquid aerosol-forming substrate may comprise at least one aerosol-former. An aerosol-former is any suitable known compound or mixture of compounds that, in use, facilitates formation of a dense and stable aerosol and that is substantially resistant to thermal degradation at the temperature of operation of the system. Suitable aerosol-formers are well known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Aerosol formers may be polyhydric alcohols or mixtures thereof, such as triethylene glycol, 1,3-butanediol and glycerine. The liquid aerosol-forming substrate may comprise other additives and ingredients, such as flavourants.

The aerosol-forming substrate may comprise nicotine and at least one aerosol former. The aerosol former may be glycerine. The aerosol-former may be propylene glycol. The aerosol former may comprise both glycerine and propylene glycol. The aerosol-forming substrate may have a nicotine concentration of between about 2% and about 10%.

Although reference is made to liquid aerosol-forming substrates above, it will be clear to one of ordinary skill in the art that other forms of aerosol-forming substrate may be used with other example embodiments. For example, the aerosol-forming substrate may be a solid aerosol-forming substrate. The aerosol-forming substrate may comprise both solid and liquid components. The aerosol-forming substrate may comprise a tobacco-containing material containing volatile tobacco flavour compounds which are released from the substrate upon heating. The aerosol-forming substrate may comprise a non-tobacco material. The aerosol-forming substrate may further comprise an aerosol former. Examples of suitable aerosol formers are glycerine and propylene glycol.

If the aerosol-forming substrate is a solid aerosol-forming substrate, the solid aerosol-forming substrate may comprise, for example, one or more of: powder, granules, pellets, shreds, spaghettis, strips or sheets containing one or more of: herb leaf, tobacco leaf, fragments of tobacco ribs, reconstituted tobacco, homogenised tobacco, extruded tobacco, cast leaf tobacco and expanded tobacco. The solid aerosol-forming substrate may be in loose form, or may be provided in a suitable container or cartridge. Optionally, the solid aerosol-forming substrate may contain additional tobacco or non-tobacco volatile flavour compounds, to be released upon heating of the substrate. The solid aerosol-forming substrate may also contain capsules that, for example, include the additional tobacco or non-tobacco volatile flavour compounds and such capsules may melt during heating of the solid aerosol-forming substrate.

As used herein, homogenised tobacco refers to material formed by agglomerating particulate tobacco. Homogenised tobacco may be in the form of a sheet. Homogenised tobacco material may have an aerosol-former content of greater than 5% on a dry weight basis. Homogenised tobacco material may alternatively have an aerosol former content of between 5% and 30% by weight on a dry weight basis. Sheets of homogenised tobacco material may be formed by agglomerating particulate tobacco obtained by grinding or otherwise comminuting one or both of tobacco leaf lamina and tobacco leaf stems. Alternatively, or in addition, sheets of homogenised tobacco material may comprise one or more of tobacco dust, tobacco fines, and other particulate tobacco by-products formed during, for example, the treating, handling, and shipping of tobacco. Sheets of homogenised tobacco material may comprise one or more intrinsic binders, that is tobacco endogenous binders, one or more extrinsic binders, that is tobacco exogenous binders, or a combination thereof to help agglomerate the particulate tobacco; alternatively, or in addition, sheets of homogenised tobacco material may comprise other additives including, but not limited to, tobacco and non-tobacco fibres, aerosol-formers, humectants, plasticisers, flavourants, fillers, aqueous and non-aqueous solvents and combinations thereof.

Optionally, the solid aerosol-forming substrate may be provided on or embedded in a thermally stable carrier. The carrier may take the form of powder, granules, pellets, shreds, spaghettis, strips or sheets. Alternatively, the carrier may be a tubular carrier having a thin layer of the solid substrate deposited on its inner surface, or on its outer surface, or on both its inner and outer surfaces. Such a tubular carrier may be formed of, for example, a paper, or paper like material, a non-woven carbon fibre mat, a low mass open mesh metallic screen, or a perforated metallic foil or any other thermally stable polymer matrix.

The solid aerosol-forming substrate may be deposited on the surface of the carrier in the form of, for example, a sheet, foam, gel or slurry. The solid aerosol-forming substrate may be deposited on the entire surface of the carrier, or alternatively, may be deposited in a pattern in order to provide a non-uniform flavour delivery during use.

According to some example embodiments, there is provided a kit for an electrically heated aerosol-generating system, the kit comprising an aerosol-generating device as described above, and a plurality of consumable cartridges for use in the aerosol-generating device, each of the cartridges comprising a storage portion containing an aerosol-forming substrate and having a fluid permeable internal surface surrounding an open-ended passage extending through the cartridge.

As used herein, the terms 'upstream' and 'downstream' are used to describe the relative positions of components, or portions of components, of cartridges, aerosol-generating devices, and aerosol-generating systems in relation to the direction of air drawn through the cartridges, aerosol-generating devices, and aerosol-generating systems during use thereof. The terms 'distal' and 'proximal', are used to describe the relative positions of components of aerosol-generating devices and aerosol-generating systems in relation to their connection to the device, such that the proximal end of a component is at the 'fixed' end which is connected to the device, and the distal end is at the 'free' end, opposite to the proximal end. Where a component is connected to the device at the downstream end of the component, the downstream end may be considered as the 'proximal' end, and vice versa.

As used herein, the terms "longitudinal" and "length" refer to the direction between the opposed ends of the cartridge, the device, or a component of the device, such as between its downstream or proximal end and the opposed upstream or distal end. The term "transverse" is used to describe the direction perpendicular to the longitudinal direction.

The upstream and downstream ends of the cartridge and the aerosol-generating device are defined with respect to the airflow when a negative pressure is applied to the mouth end of the aerosol-generating device. Air is drawn into the cartridge or the device at its upstream end, passes downstream through the cartridge or the device and exits the cartridge or device at its downstream end.

As used herein, the term "air inlet" is used to describe one or more apertures through which air may be drawn into the aerosol-generating system.

As used herein, the term "air outlet" is used to describe one or more aperture through which air may be drawn out of the aerosol-generating system.

It should be understood that the features described in relation to one or more example embodiments may equally be applied to other relevant example embodiments of the disclosure although not explicitly set forth herein. For instance, the features described in relation to the aerosol-generating device may be equally applied to the aerosol-generating system and the kit, and vice versa.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

Figure 1:
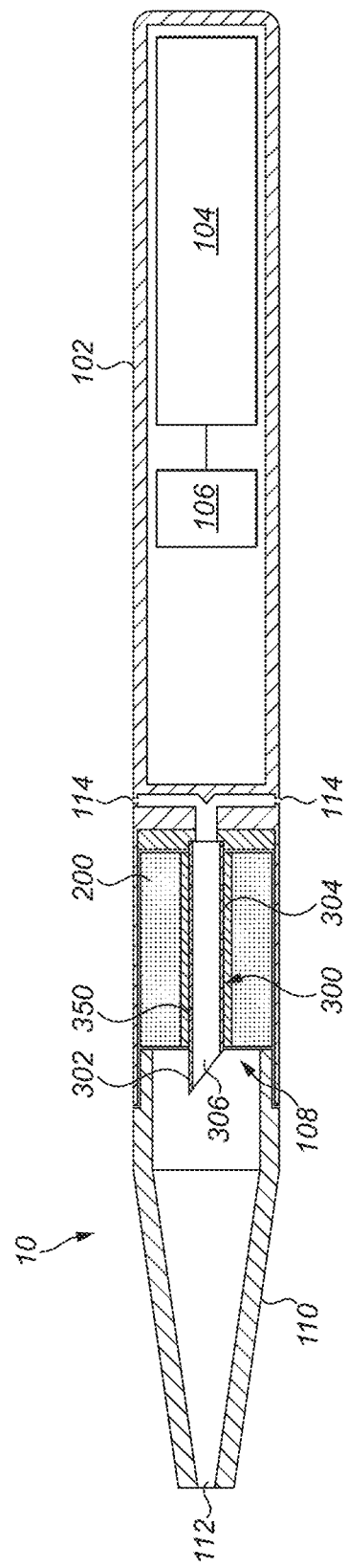
FIG. 1 illustrates a longitudinal cross-section of an aerosol-generating system according to an example embodiment.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

FIG. 1 is a schematic illustration of an aerosol-generating system 10 according to an example embodiment comprising an aerosol-generating device 100 and an aerosol-generating article in the form of a cartridge 200 (e.g., consumable cartridge).

The aerosol-generating device 100 comprises a housing 102 (e.g., main housing) containing a battery 104 and control electronics 106. The housing 102 also defines a cavity 108 into which the cartridge 200 is received. The aerosol-generating device 100 further includes a mouthpiece portion 110 including an outlet 112. In this example, the mouthpiece portion 110 is connected to the housing 102 by a screw fitting, but any suitable kind of connection may be used, such as a hinged connection or a snap fitting. The aerosol-generating device 100 further includes a heater assembly 300 comprising a piercing member 302 (e.g., elongate piercing member) in the form of a hollow shaft portion 304 connected to the housing 102 and a plurality of electric heaters 350 spaced apart along the length of the hollow shaft portion 304. The heater assembly 300 is positioned centrally within the cavity 108 of the aerosol-generating device 100 and extends along the longitudinal axis of the cavity 108. The hollow shaft portion 304 defines an airflow passage 306. Air inlets 114 are provided in the housing 102 upstream of the heater assembly 300 and are in fluid communication with the outlet 112 via the airflow passage 306.

Figure 2:
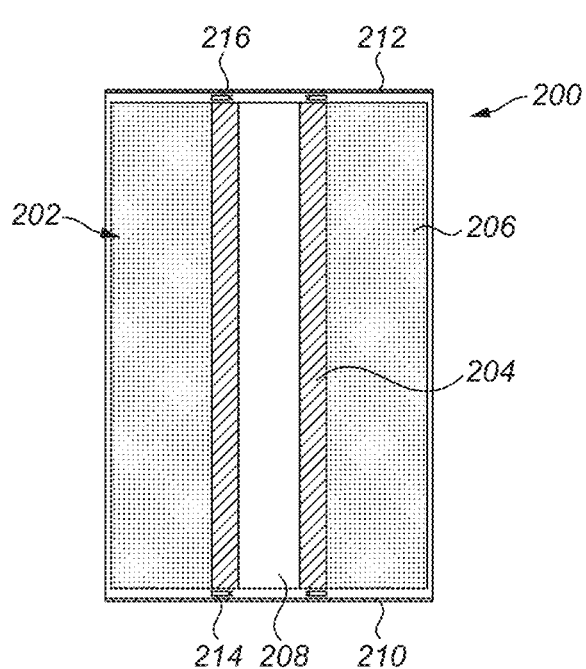
FIG. 2 illustrates a longitudinal cross-section of a consumable cartridge for use with the aerosol-generating system of FIG. 1.

As best seen in FIG. 2, the cartridge 200 comprises a storage portion 202 including a capillary wick 204 (e.g., tubular capillary wick) surrounded by a capillary material 206 (e.g., tubular capillary material) containing liquid aerosol-forming substrate. The cartridge 200 has a hollow cylindrical shape through which extends an internal passageway 208. The capillary wick 204 surrounds the internal passageway 208 so that the internal passageway 208 is at least partly defined by an inner surface of the capillary wick 204. The upstream and downstream ends of the cartridge 200 are capped by frangible seals 210, 212. The cartridge 200 further includes a sealing ring 214, 216 at each of the upstream and downstream ends of the internal passageway 208.

Figure 3A:
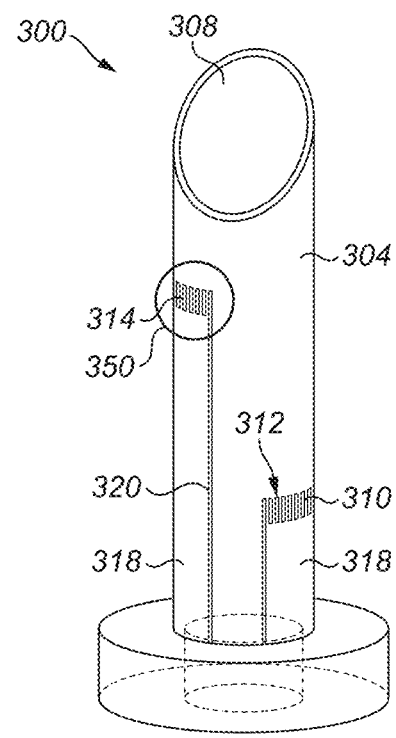
FIG. 3A illustrates a perspective view of an example embodiment of a heater assembly for the aerosol-generating system of FIG. 1.
Figure 3B:
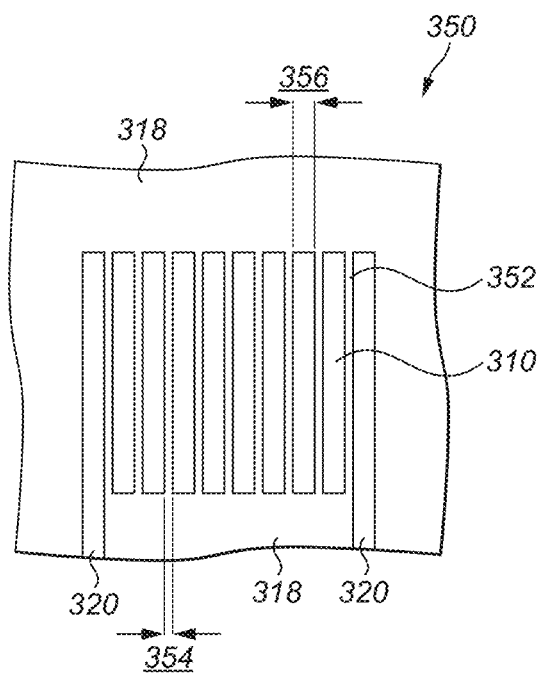
FIG. 3B illustrates an enlarged, partial side view of the heater assembly of FIG. 3A.

As best seen in FIGS. 3A and 3B, the hollow shaft portion 304 of the heater assembly 300 has a piercing surface 308 at its distal, or downstream end. In this example, the piercing surface 308 is formed by a sharp tip at the distal end of the hollow shaft portion 304. The hollow shaft portion 304 comprises a plurality of apertures 310 and partially divided into a plurality of electrically isolated sections 318 which are separated from each other by gaps 320 (e.g., insulating gaps). The plurality of apertures are arranged in a plurality of groups of apertures spaced apart along the length of the hollow shaft portion. In this example, the apertures are arranged in a first group 312 towards the proximal end of the hollow shaft portion 304 and a second group 314 towards the distal end of the hollow shaft portion 304. Each of the groups of apertures defines an electric heater 350. As shown in FIG. 3B, each electric heater 350 comprises a plurality of heating elements 352 defined by narrow regions of the hollow shaft portion between adjacent apertures 310. The heating elements 352 have a width 354 and the apertures have a width 356. The width 356 of the apertures may be selected so that, when in use, liquid aerosol-forming substrate is drawn in to the electric heater 350 by capillary action through the apertures 310. In the example shown in FIG. 3A, the first and second groups of apertures 310 are offset around the circumference of the hollow shaft portion 304. In other examples, two or more of the groups of apertures 310 may be aligned around the circumference of the hollow shaft portion 304.

The hollow shaft portion 304 is at least partially divided into a plurality of electrically isolated sections 318 which are electrically connected to the battery in the device. The heating elements 352 are connected at one end to one of the electrically isolated sections 318 and at the other end to a different one of the electrically isolated sections. In this manner, the electric heaters 350 are electrically connected to the device. The electrically isolated sections 318 may be electrically isolated from each other by the gaps 320. Thus, the electric heaters 350 may be electrically isolated from the each other to allow separate operation, control, or monitoring, without the need for separate electrical wiring for each heater. In this example, the gaps 320 are air gaps. That is, the gaps 320 do not contain insulating material. In other examples, one or more of the gaps 320 may be filled or partially filled with an electrically insulating material.

Figure 4:
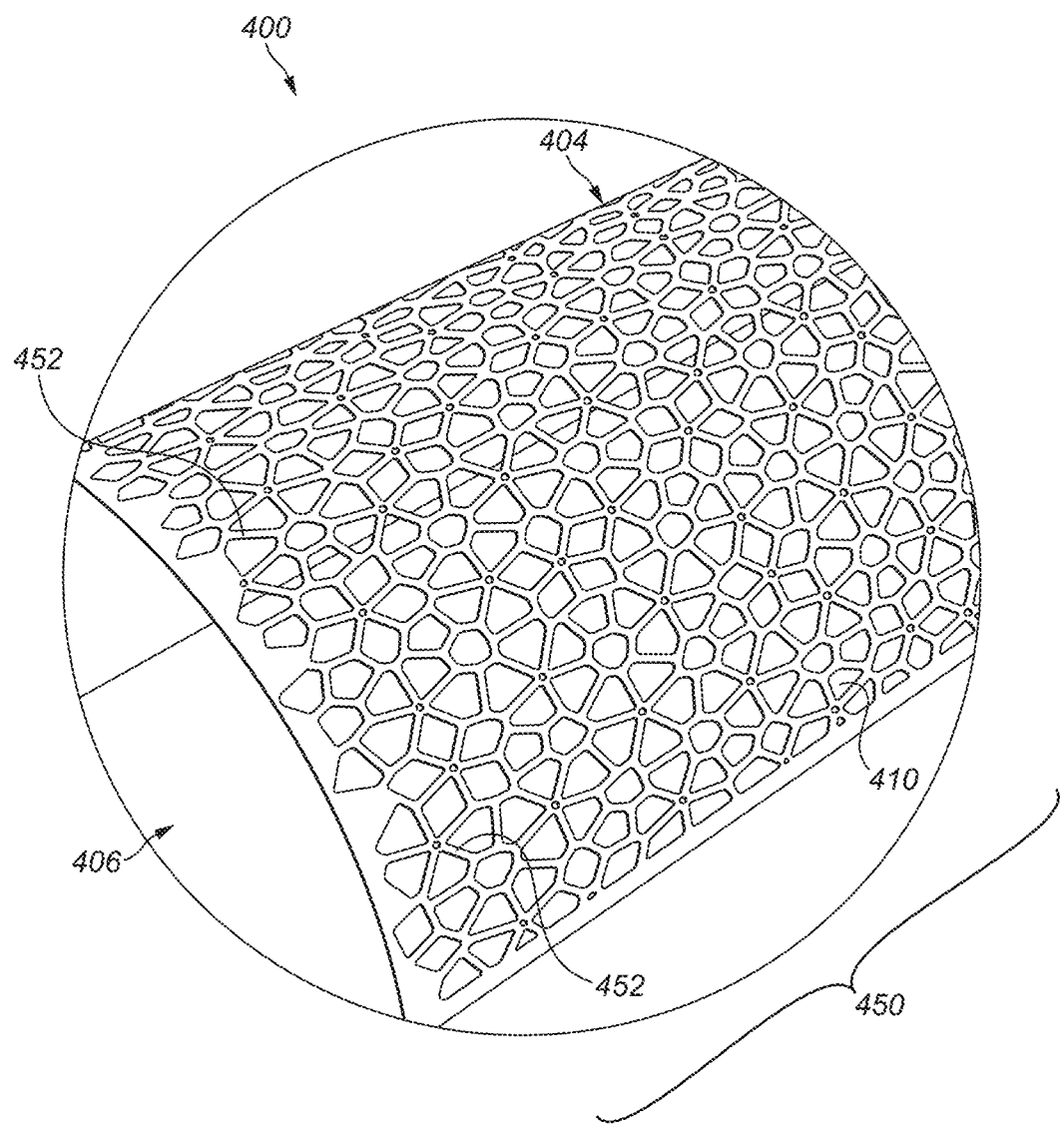
FIG. 4 illustrates an enlarged, partial perspective view of an example embodiment of a heater assembly for the aerosol-generating system of FIG. 1.

FIG. 4 illustrates a partial view of a heater assembly 400 according to an example embodiment. As with the heater assembly 300, the heater assembly 400 comprises an elongate piercing member in the form of a hollow shaft portion 404 defining an airflow passage 406 and having a plurality of apertures 410 along its length. However, unlike the heater assembly 300, the heater assembly 400 comprises a single electric heater 450 extending along substantially the entire length of the hollow shaft portion 404 and circumscribing the hollow shaft portion 404. The electric heater 450 again comprises a plurality of heating elements 452 defined by narrow regions of the hollow shaft portion 404 between adjacent apertures 410. However, in the case of heater assembly 400, the heating elements 452 are in a mesh pattern.

Figure 5A:
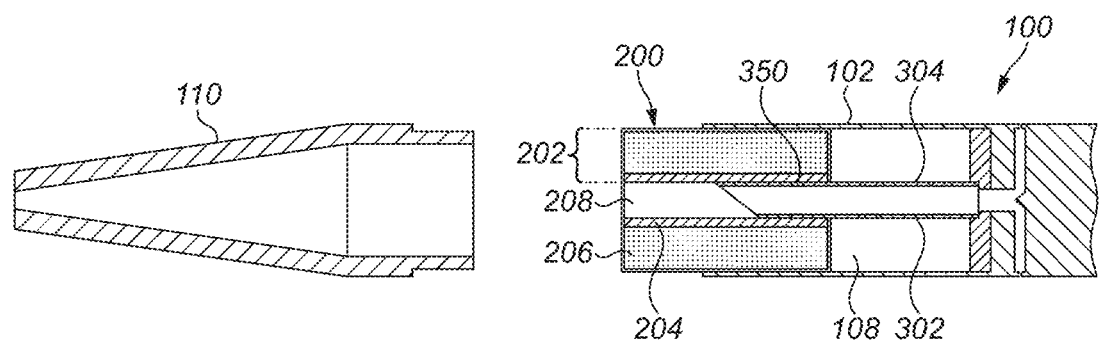
FIGS. 5A and 5B illustrate a method of inserting a consumable cartridge into the aerosol-generating device of the aerosol-generating system of FIG. 1.
Figure 5B:
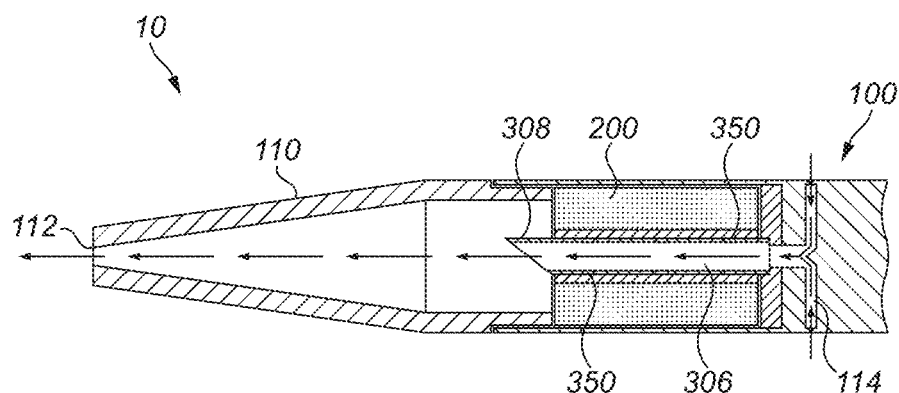

Referring to FIGS. 5A and 5B, insertion of the cartridge 200 into the aerosol-generating device 100 of the aerosol-generating system 10 will now be described.

To insert the cartridge 200 into the aerosol-generating device 100, and thereby assemble the aerosol-generating system 10, the first step is to remove the mouthpiece portion 110 from the housing 102 of the aerosol-generating device 100 and to insert the cartridge 200 into the cavity 108 of the aerosol-generating device 100, as shown in FIG. 5A. During insertion of cartridge 200 into the cavity 108, the piercing surface 308 at the distal end of the piercing member 302 breaks the frangible seal at the upstream end of the cartridge 200. As the cartridge 200 is inserted further into the cavity 108 and the piercing member 302 extends further into the internal passageway 208 of the cartridge, the piercing surface 308 engages with and breaks through the frangible seal at the downstream end of the cartridge 200 to create a hole in the frangible seal.

The cartridge 200 is then fully inserted into the cavity 108 and the mouthpiece portion 110 is replaced onto the housing 102 and engaged thereto to enclose the cartridge 200 within the cavity 108, as shown in FIG. 5B. When the cartridge 200 is fully inserted into the cavity 108, the holes in the frangible seals at the upstream and downstream ends of the cartridge 200 each have a diameter approximately equal to the outer diameter of the hollow shaft portion 304. The sealing rings at the upstream and downstream ends of the cartridge 200 form a seal around the hollow shaft portion 304. Together with the frangible seals this reduces or prevents leakage of liquid aerosol-forming substrate from the cartridge 200 and out of the aerosol-generating system 10. The cartridge 200 may be pressed fully into the cavity 108 before the mouthpiece portion 110 is replaced onto the housing 102. Alternatively, the cartridge 200 may be partially inserted into the cavity 108 and the mouthpiece portion 110 used to push the cartridge 200 into the cavity 108 until it is fully inserted.

As shown in FIG. 5B, when the cartridge 200 is fully inserted into the cavity 108 of the aerosol-generating device 100, an airflow pathway, shown by arrows in FIG. 5B, is formed through the aerosol-generating system 10. The airflow pathway extends from the air inlets 114 to the outlet 112 via the internal passageway 208 in the cartridge 200 and the airflow passage 306 in the heater assembly 300. As also shown in FIG. 5B, when the cartridge 200 is fully inserted, the electric heaters 350 are in fluid communication with the storage portion 202 of the cartridge 200 at the inner surface of the internal passageway 208.

In use, liquid aerosol-forming substrate is transferred from the storage portion 202 to the electric heaters 350 and may be held in the apertures of each electric heater 350 by capillary action. In this example, the outer diameter of the hollow shaft portion 304 is greater than the inner diameter of the internal passageway 208 of the cartridge 200 so that the storage portion 202 of the cartridge 200 is compressed by the hollow shaft portion 304. This ensures direct contact between the electric heaters 350 and the storage portion 202 to help transfer of liquid aerosol-forming substrate to the electric heaters 350. The battery supplies electrical energy to the heating elements of each electric heater 350. The heating elements heat up to vaporise liquid substrate in the capillary wick 204 to create a supersaturated vapour. At the same time, the liquid being vaporised is replaced by further liquid moving along the capillary wick 204 of the liquid storage portion 202 by capillary action. (This is sometimes referred to as "pumping action".) When a negative pressure is applied to the mouthpiece portion 110, air is drawn through the air inlets 114, through the airflow passage of the hollow shaft portion 304, past the electric heaters 350, into the mouthpiece portion 110 and out of the outlet 112. The vaporised aerosol-forming substrate is entrained in the air flowing through the airflow passage of the hollow shaft portion 304 and condenses within the mouthpiece portion 110 to form an inhalable aerosol, which is carried towards the outlet 112.

The device may be operated by a manually-operated switch (not shown) on the aerosol-generating device 100. Alternatively, or in addition, the device may include a sensor for detecting a puff. When a puff is detected by the sensor, the control electrics control the supply of electrical energy from the battery to the electric heaters 350. The sensor may comprise one or more separate components. In some examples, the puff sensing function is performed by the heating elements of the heater and wick assemblies. For example, by measuring with the control electronics one or more electrical parameters of the heating elements and detecting a particular change in the measured electrical parameters which is indicative of a puff.

During use of the system, the distribution of liquid aerosol-forming substrate in the cartridge may change. For example, as the liquid aerosol-forming substrate in the storage portion is depleted during use, or where the system is held at an angle for a sufficient period of time. This change in the distribution of liquid aerosol-forming substrate may lead to differences in the amount of liquid in the capillary body of each electric heater and, consequently, the temperature of the heating element of each electric heater. This is discussed below in relation to FIG. 5C.

Figure 5C:
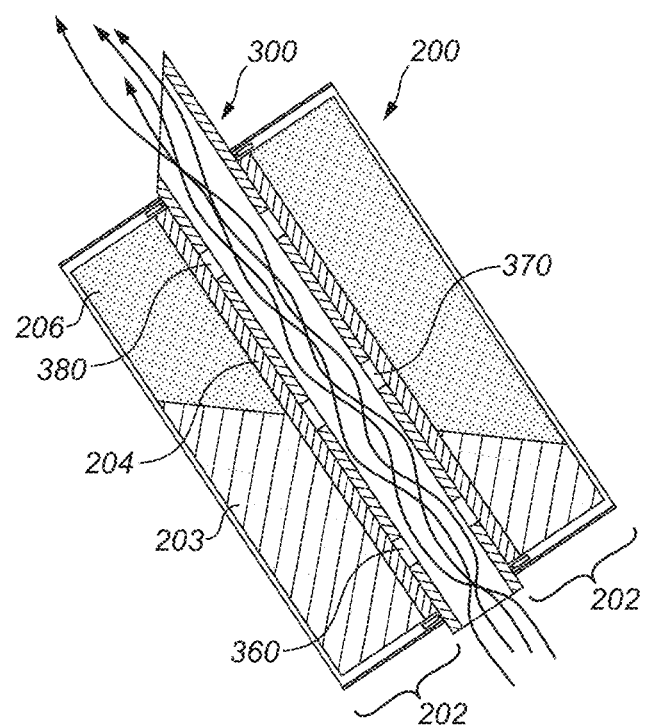
FIG. 5C illustrates a longitudinal cross-section of the cartridge and heater assembly of the system of FIGS. 5A and 5B in which the aerosol-generating system is held in a tilted position.

FIG. 5C shows a longitudinal cross-section of the cartridge 200 and heater assembly 300 of the aerosol-generating system following a period in which the system has been held in a tilted position. As shown, the remaining liquid 203 in the cartridge 200 has settled in the storage portion 202 at an angle to the heater assembly 300. As the electric heaters are spaced apart along the length of the cartridge 200, the amount of liquid aerosol-forming substrate in the region of storage portion 202 adjacent to the electric heaters is not uniform. In particular, the region of storage portion 202 at the upstream end of the cartridge adjacent to a first pair of electric heaters 360 is saturated with liquid aerosol-forming substrate, while the region of storage portion 202 adjacent to a second pair of electric heaters 370 midway along the length of the heater assembly 300 is only partially wet with liquid aerosol-forming substrate, and the region of storage portion 202 adjacent to a third pair of electric heaters 380 at the downstream end of the heater assembly 300 is dry. Consequently, the electric heaters 360, 370, 380 may be caused to run at different temperatures. As the electrical parameters of each electric heater, such as the electrical resistivity of the heating element, may vary as a function of the temperature, the distribution of the liquid aerosol-forming substrate or the remaining amount of liquid aerosol-forming substrate may be estimated by the control circuitry through measuring the electrical parameters of each electric heater. The control electronics is configured to separately measure one or more electrical parameters of each electric heater during use and to calculate an estimated remaining amount, or estimated distribution, of liquid aerosol-forming substrate in the cartridge based on differences in the measured electrical parameters from the electric heaters. Thus, the electric heaters function both as heaters and as sensors.

The device includes an indicator (not shown), such as a display or audio or haptic output, connected to the control circuitry, which may be used to convey information regarding the estimated remaining amount of liquid aerosol-forming substrate in the cartridge 200. When the estimated remaining amount falls below a threshold level, the electric circuitry may also be configured to operate the indicator to provide an alert and prompt the replacement of the cartridge. The control circuitry may also be configured to estimate the distribution of liquid aerosol-forming substrate in the cartridge based on differences in the measured electrical parameters from the electric heaters and to operate the indicator, when the estimated distribution suggests that system has been held at a particular angle for too long, to provide an alert that the orientation of the aerosol-generating device 100 should be altered, at least temporarily, to allow the liquid aerosol-forming substrate to be redistributed in the storage portion. In this, or other examples, the control circuitry may be configured to provide an alert about the estimated remaining amount or estimated distribution via a communication link with a separate device, such as a smartphone, swart-watch, tablet, desktop computer, or similar device.

In addition to detecting differences in electrical parameters in the electric heaters and calculating an estimated remaining amount, or estimated distribution, of liquid aerosol-forming substrate in the cartridge 200, the control electronics 106 is also configured to control the supply of electrical power to each of the electric heaters in response to the estimated remaining amount, or estimated distribution. In particular, where the measured electrical parameters indicate that one or more of the electric heaters is partially dry, the control electronics 106 is configured to reduce the supply of electrical energy to that electric heater. This allows the aerosol-generating system 10 to determine which of the electric heaters is in the best condition to generate aerosol in the most effective way. This allows adverse changes to the properties of aerosol generated by the aerosol-generating system 10, caused by variations in wetness and temperature across the electric heaters, to be minimised. It may also reduce energy consumption of the aerosol-generating system 10, and reduce the risk of damage to the electric heaters due to overheating. Where the electrical parameters indicate that one or more of the electric heaters is dry, the control electronics 106 is configured to reduce the supply of electrical energy to that electric heater to zero.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. An aerosol-generating system, comprising:
a cartridge including a storage portion containing at least one aerosol-forming substrate, the storage portion defining an internal passage extending through the cartridge; and
an aerosol-generating device including a housing and a heater assembly, the housing defining a cavity configured to receive at least a portion of the cartridge, the heater assembly positioned within the cavity of the housing and including a hollow shaft portion configured to extend into the internal passage of the cartridge, the hollow shaft portion having at least one heater integrally formed therewith, the at least one heater including at least one heating element configured to heat the at least one aerosol-forming substrate, the storage portion being compressible and a diameter of the internal passage being less than an outer diameter of the hollow shaft portion, the hollow shaft portion configured to pierce the storage portion of the cartridge during insertion of the cartridge into the cavity.

2. The aerosol-generating system according to claim 1, wherein the at least one aerosol-forming substrate includes an aerosol-forming liquid.

3. The aerosol-generating system according to claim 1, wherein the at least one aerosol-forming substrate includes an aerosol-forming solid.

4. The aerosol-generating system according to claim 2, wherein the internal passage of the storage portion is fluid permeable and includes a capillary wick configured to transport the aerosol-forming liquid to the heater assembly.

5. The aerosol-generating system according to claim 1, wherein the cartridge and the aerosol-generating device are removably coupled.

6. The aerosol-generating system according to claim 1, wherein the storage portion includes a frangible seal configured to be pierced by the hollow shaft portion during insertion of the cartridge into the cavity.

7. An aerosol-generating device, comprising:
a housing defining a cavity configured to receive a cartridge containing an aerosol-forming substrate; and
a heater assembly within the cavity of the housing, the heater assembly including a hollow shaft portion including at least one heater integrally formed therewith and a plurality of apertures offset around or aligned around a circumference thereof.

8. The aerosol-generating device of claim 7, wherein the hollow shaft portion
has a piercing tip and is configured to extend into the cartridge via the piercing tip when the cartridge is received in the cavity, and
defines an airflow passage that is part of an airflow pathway through the aerosol-generating device.

9. The aerosol-generating device according to claim 7, wherein the heater assembly is fixedly connected within the cavity defined by the housing of the aerosol-generating device.

10. The aerosol-generating device according to claim 7, wherein
the at least one heater includes at least one heating element comprising one or more narrow regions of the hollow shaft portion between adjacent apertures of the plurality of apertures.

11. The aerosol-generating device according to claim 7, wherein a width of the plurality of apertures is configured to draw the aerosol-forming substrate into the at least one heater by capillary action.

12. The aerosol-generating device according to claim 7, wherein the plurality of apertures is arranged in a plurality of groups of apertures spaced apart along a length of the hollow shaft portion.

13. The aerosol-generating device according to claim 7, wherein the housing of the aerosol-generating device further comprises a removable mouthpiece portion comprising at least one air outlet and one air inlet.

14. The aerosol-generating device according to claim 13, wherein
the cavity of the housing is configured to partially receive the cartridge housing when the removable mouthpiece portion is removed, and
and the removable mouthpiece portion is configured to push the cartridge into the cavity until the cartridge is fully inserted when the removable mouthpiece portion is replaced onto the housing.

15. The aerosol-generating device according to claim 7, wherein the at least one heater circumscribes the hollow shaft portion.

16. The aerosol-generating device according to claim 7, wherein the at least one heater extends along a length of the hollow shaft portion.

17. The aerosol-generating device according to claim 7, wherein the at least one heater is in a form of a plurality of electric heaters spaced apart along a length of the hollow shaft portion.

18. The aerosol-generating device according to claim 17, wherein the plurality of electric heaters are electrically isolated from each other to permit independent heating.

19. The aerosol-generating device according to claim 17, wherein the hollow shaft portion is at least partially divided into a plurality of electrically isolated sections for coupling the plurality of electric heaters to an electrical power supply, the electrically isolated sections being electrically isolated from each other by one or more insulating gaps in the hollow shaft portion.

* * * * *